United States Patent [19]

Mezrich et al.

[11] 4,131,021
[45] Dec. 26, 1978

[54] HIGH RESOLUTION PULSE-ECHO ULTRASONIC-IMAGING DISPLAY SYSTEM

[75] Inventors: Reuben S. Mezrich, Rocky Hill; Edwin T. Koenig, Spring Lake Heights, both of N.J.

[73] Assignee: RCA Corporation, New York, N.Y.

[21] Appl. No.: 766,564

[22] Filed: Feb. 7, 1977

[30] Foreign Application Priority Data

Mar. 4, 1976 [GB] United Kingdom ............... 08660/76
Jul. 16, 1976 [GB] United Kingdom ............... 29766/76

[51] Int. Cl.² .......................................... G01N 29/00
[52] U.S. Cl. ........................................ 73/606; 73/625; 73/629
[58] Field of Search ............ 73/67.5 R, 67.7, 67.8 R, 73/67.8 S, 67.9, 71.5, 606, 607, 625, 614, 632, 626, 641, 642, 629; 340/5 MP, 5 H, 8 FT; 128/2 V, 2.052

[56] References Cited

U.S. PATENT DOCUMENTS

| | | | |
|---|---|---|---|
| 2,833,999 | 5/1958 | Howry | 73/642 |
| 3,817,089 | 6/1974 | Eggleton et al. | 73/623 |
| 3,862,578 | 1/1975 | Schlutter | 73/623 |
| 3,886,490 | 5/1975 | Green | 340/5 MP |
| 3,895,340 | 7/1975 | Gilmour | 340/5 MP |
| 3,895,525 | 7/1975 | Eichelberger et al. | 340/5 MP |
| 3,913,061 | 10/1975 | Green | 73/633 |
| 3,918,024 | 11/1975 | Macovski | 340/5 MP |
| 3,918,297 | 11/1975 | Rocha | 73/607 |
| 3,937,066 | 2/1976 | Green et al. | 340/5 MP |
| 4,016,750 | 4/1977 | Green | 73/629 |

*Primary Examiner*—Stephen A. Kreitman
*Attorney, Agent, or Firm*—H. Christoffersen; Samuel Cohen; George J. Seligsohn

[57] ABSTRACT

An acoustic focusing device occupying a fixed aperture is used to both illuminate internal structure of a visually opaque object with a scanning focused beam of ultrasonic energy and for returning a reflected signal portion of the scanning focused beam passed therethrough for detection. The use of such a fixed-aperture focusing device permits deep soft tissue of a living human being to be displayed with high resolution for medical diagnostic purposes in a manner compatible with a real time frame rate.

9 Claims, 16 Drawing Figures

HIGH RESOLUTION PULSE-ECHO ULTRASONIC-IMAGING DISPLAY SYSTEM

Reference should be made to the following related U.S. patent applications, filed concurrently herewith and assigned to the same assignee as the present application:

Ser. No. 766,565, — Mezrich and Anderson; Ser. No. 766,527, — Mezrich; Ser. No. 766,528 — Mezrich and Vilkomersen; Ser. No. 766,526 — Mezrich and Avins.

This invention relates to ultrasonic imaging of the interior of visually opaque objects and, more specifically, to a high-resolution pulse-echo imaging technique which is particularly suitable for use in imaging of soft tissue (including deep soft tissue) of a living human being for medical diagnostic purposes, as well as for non-destructive examination of inanimate objects.

Reference is made to the paper "Considerations for Diagnostic Ultrasonic Imaging", by Green, et al., of the Stanford Research Institute, appearing on pages 97–111 of *Acoustical Holography*, Volume 4, Proceedings of the Fourth International Symposium, April 1972, edited by Glen Wade and published by Plenum Press, New York in 1972. This paper, which discusses both pulse-echo ultrasonic-imaging and focused and holographic ultrasonic imaging for use as a non-toxic and non-invasive diagnostic tool for soft tissue, compares the desirable features which ought to be incorporated in a diagnostic ultrasonic imaging system with the state of the ultrasonic imaging art at that time. One of the conclusions made in this paper is that the tightly inter-related sensitivity, resolution and operating frequency parameters realizable with any imaging system then under consideration would be of quite limited diagnostic use (especially for examining deep tissue, such as abdominal and pelvic organs or viewing the heart), although such systems were practical for pathological examinations of excised organs.

A more recent study of the state of the art of ultrasonic imaging of soft tissue within a living human being for medical diagnostic purposes appears in the article "Ultrasonic Imaging", by C. R. Hill, pages 153–162 of the March, 1976 (Volume 9, No. 3) of Journal of Physics E, *Scientific Instruments*, published by the Institute of Physics. This article brings out the fact that the majority of practical ultrasonic imaging systems currently in use are based on the pulse-echo approach, and current technology is moving away from simple outlining of major echo-producing interfaces and towards more detailed imaging of fine structure of organs and tissues, in a gray-scale display format. Although this article does not indicate that high resolution (e.g. in the range of 0.5–2.5 mm) of deep tissue is obtainable with pulse-echo ultrasonic imaging, it does recognize that it is highly desirable to provide practical imaging systems which incorporate rapid image scanning techniques so that the image may be viewed in a time which, at least, approaches real time or, preferably, is at real time itself. In this regard, the articles states that such rapid scanning techniques can be achieved by either (1) physical movement of the ultrasonic transducer itself or (2) electrical manipulation of the beam axis of a multi-element transducer array (i.e. by selective use of different single elements or different sub-groups of elements).

As known in the ultrasonic imaging art, the resolution capability increases with increasing ultrasonic frequency, but the attenuation by absorption experienced by ultrasonic energy propagating through a medium, such as water or human tissue, also increases with frequency. In quantitative terms, the absorption coefficient for most soft tissue is in the range between $0.5 \times f$ and $2.5 \times f$ (with f being the value of the ultrasonic frequency in MHz) db/cm (with a value of $1 \times f$ db/cm being typical). In practice, in order to avoid an undue amount of attenuation, the frequency of the ultrasonic wave energy is normally selected to be in a range from 1–10 MHz (depending upon the particular propagating medium and the total distance to be traveled within the propagating medium). A reasonable trade-off between resolution and attenuation for observation of deep tissue is an ultrasonic frequency in the range of 2–3 MHz.

It also has been suggested in the diagnostic ultrasonic imaging art that the maximum safe average ultrasonic intensity incident on a human subject should be limited to be no more than $10^{-2}$ watts/cm$^2$, while the maximum safe peak ultrasonic intensity should be no greater than 0.5 watts/cm$^2$. Thus, at maximum peak power, the pulse duty cycle can be no greater than 2% (e.g. a pulse repetition rate no higher than 20 KHz for 1$\mu$s transmitted pulses). The minimum receiver sensitivity required for detecting receive pulse echoes is determined by this maximum allowable incident ultrasonic intensity and by the total amount of attenuation experienced by ultrasonic wave energy in propagating to and from the imaged tissue through the intervening tissue. Commercially available clinical instruments, which at this time provide only limited focusing, cannot image deep tissue with an achievable resolution much below one centimeter.

However, U.S. Pat. No. 3,958,559, issued on May 25, 1976 to Glenn et al., discloses the use of a relatively large aperture lens (specifically, an elliptical-shaped lens) for converging a relatively wide-area incident beam of ultrasonic wave energy to a selected diffraction-limited focused spot having a spot diameter which may be as small as 0.5 mm at the target. The fact that the converging beam covers a relatively large area, compared to the size of the focused spot, as it enters the body of a human being, and that the energy therein undergoes absorption as it converges toward the small focused spot of the target, would permit, in principle, a sufficient amount of energy to reach the target spot to achieve a relatively high-resolution ultrasonic image without exceeding the safe maximum limits of ultrasonic intensity incident on the human being. However, in the system disclosed in this patent, the position of the selected spot is scanned over a relatively large area with respect to the spot area by means of a scanner, which is capable of mechanically moving a unitary transducer and lens assembly both in and out along the acoustic axis, and up and down transversely to the axis. The need to mechanically move a large aperture lens with respect to the target area creates problems in the achievement of the high resolution capability of a large aperture lens at rapid scanning rates, due to the inherent inertia of any mechanical scanning arrangement for moving a large aperture lens. In addition, it is difficult and expensive to mount such a mechanically scannable unitary transducer and lens assembly with a rigidity sufficient to achieve the high resolution capability of the large aperture lens. Another relatively complex mechanical ultrasonic scanning apparatus for medical diagnostic purposes, which does not use a lens, is disclosed in U.S. Pat. No. 3,752,255, issued Aug. 14, 1976 to Hill et al.

The present invention is directed to novel apparatus for use in an ultrasonic pulse-echo system capable of displaying an image of certain internal structure of visually opaque object being scanned with ultrasonic wave energy. The apparatus comprises an acoustic focusing device occupying a given aperture, which aperture remains substantially fixed in position with respect to the object while the object is being scanned. The apparatus further comprises ultrasonic beam focusing means including transducer means and beam scanning means for illustrating the certain internal structure through the focusing device with a scanning focused beam of ultrasonic wave energy. The transducer means is situated remotely from both the focusing device and the internal structure for receiving and detecting a signal portion of the focused beam reflected from the certain internal structure and returned through the focusing device to the transducer after a time delay proportional to the distance to the remotely distant transducer and the certain internal structure.

The fact that the fixed focusing device and the transducer means are remotely situated makes it possible to achieve scanning of the illuminating beam by operating on the ultrasonic wave energy, which is inertialess, rather than on the fixed aperture focusing device. This makes the present invention compatible with rapid (i.e. up to and including real time) scanning of the certain internal structure. (The term "real time", as used herein, means a frame rate for the scanning of a target region at least sufficient to follow natural movements of the target, such as those due to a patient's heartbeat, the movement of a fetus or even the heartbeat of a fetus. A frame rate of ten scans of the target area per second is normally sufficient to follow such natural movements).

Further, when the focusing device is a fixed aperture lens, scanning may be achieved by angularly displacing the axis of the incident beam of ultrasonic wave energy with respect to the acoustic axis of the fixed aperture lens. Ignoring lens aberrations, this provides a substantially flat-field image in which the linear displacement of any point in the image is substantially proportional to the angular displacement of the incident beam illuminating the fixed-aperture focusing device. In the drawings:

Figures 1, 2, 2A:
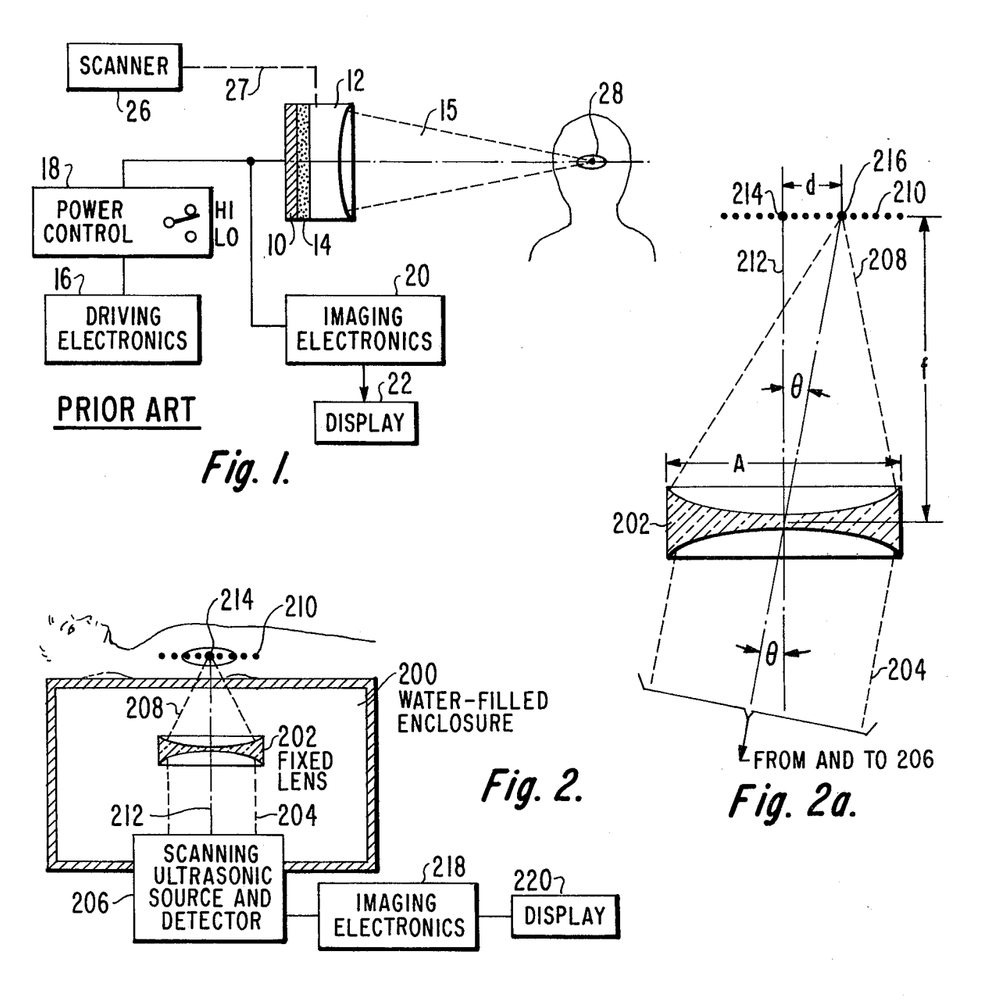
FIG. 1 shows a prior art pulse-echo ultrasonic imaging system incorporating a lens.
FIGS. 2 and 2a illustrate a pulse-echo ultrasonic imaging system embodying the present invention.

FIG. 1 shows a prior art pulse-echo ultrasonic imaging system incorporating a lens. In most respects (but not all) the arrangement shown in FIG. 1 is substantially identical to that disclosed in FIG. 3 of the aforesaid U.S. Pat. No. 3,958,559.

More specifically, ultrasonic transducer 10 is coupled to plano-concave acoustic lens 12 by the interposition of a layer 14 of suitable coupling medium such as water, or the like. The shape of the front concave surface of lens 12 need not be elliptical, as it is in the case of FIG. 3 of the aforesaid U.S. Pat. No. 3,958,559, but may be spherical or of any other appropriate shape for focusing the ultrasonic energy emanating therefrom into converging beam 15.

Transducer 10 is driven by suitable radio frequency driving electronics 16 and is operative to convert this electrical energy into ultrasonic waves, or to convert ultrasonic waves to radio frequency energy. Thus, the transducer is capable of acting both as an ultrasonic transmitting and detecting element, and for both functions desirably has as large an aperture as is feasible in order to maximize the ultrasound power output and capture angle of the echoes reflected from an object.

Converging ultrasonic beam 15 is coupled to the head by a fluid medium (not shown), usually water because of its ready availability and relative ease of handling, and focused to a small spot within focal zone 28. Transducer 10 is excited at a frequency in the range, for example, of 1–10 MHz to produce exploratory converging beam 15, when the power control 18 of the system is at the "low" position. Echo pulses detected by transducer 10 are applied to imaging electronics 20 tuned to the carrier frequency of the associated driving electronics to produce output voltage pulses, the magnitudes of which are proportional to the amplitude of the echo pulses. These pulses may be presented on an "A" scan display, or on the illustrated "C" scan display 22, on which the spot 24 depicts the locations of depth coordinates of an internal biological structure, such as a tumor, on the brain of the patient being examined.

The transducer-lens assembly, composed of transducer 10 and lens 12 coupled by medium 14 is scanned in a preselected manner by scanner 26, which is mechanically connected to the transducer-lens assembly by mechanical link 27.

In FIG. 1, the preselected manner in which the unitary transducer-lens assembly is mechanically scanned is not limited to the movement of the assembly in and out along the acoustic axis of lens 12 and up and down transversely of this axis, as specifically disclosed in the aforesaid U.S. Pat. No. 3,958,559. For instance, scanner 26 may mechanically move the unitary assembly of transducer 10 and lens 12 continuously in a conical scan, a spiral scan or a television raster scan, as examples. Alternatively, the unitary assembly of transducer 10 and lens 12 may be mechanically moved in stepped fashion to each one of a large plurality of sampling points, each of the points being imaged while the unitary assembly is stationary, the stepping of the unitary from one sampling point to the next only taking place between the imaging of each successive stationary sampling point.

Referring now to FIGS. 2 and 2a, there is shown a human patient lying on water-filled table 200. Immersed within water-filled table 200 is fixed lens 202, which is illuminated by a substantially plane wavefront beam 204 of ultrasonic energy from scanning ultrasonic source and detector 206 disposed in spaced relationship with fixed lens 202.

The term "fixed" lens, as used herein, means that the effective position of the aperture of lens 202 remains substantially stationary with respect to the human patient lying on water-filled table 200 during an image scan. However, in order to select the particular soft tissue within the human patient to be imaged, the operating distance between lens 202 and the human patient may be adjusted, if desired, prior to an image scan, by either changing the height of the top of water-filled table 200 with respect to lens 202 or by changing the position of lens 202 with respect to the top of water-filled table 200, without departing from the above definition of "fixed" lens. Further, since the mere rotation of a circularly symmetrical lens about its own axis has no effect at all on the position of the lens aperture or the way the lens acts on ultrasonic energy transferred therethrough, such mere rotation of the lens about its own axis is to be construed as to be within the above definition of the term "fixed" lens. Fixed lens 202 transfers the ultrasonic energy in plane wavefront beam 204 incident thereon into converging beam 208, which focuses at a small spot of focal plane 210 of lens 202 (located within the body of the human patient).

FIG. 2 shows plane-wavefront illuminating beam 204 of ultrasonic energy at a point in its scan where its direction of travel is parallel to acoustic axis 212 of fixed lens 202. In this case, ultrasonic energy converging beam 208 emerging from fixed lens 202 focuses at a spot centered at focal point 214 in focal plane 210 of lens 202. However, as shown in FIG. 2a, when plane wavefront illuminating beam 204 is at a point in its scan where its direction of travel is angularly displaced by angle $\theta$ from acoustic axis 212 of lens 202, converging beam 208 emerging from lens 202 focuses at a spot centered at point 216 in focal plane 210 of lens 202. As shown in FIG. 2a, point 216 is linearly displaced by a distance d from focal point 214. As is known in the optical art, the relationship between the distance d and the angular displacement $\theta$ is given by the following equation:

$$d = f\theta, \qquad (1)$$

where f is the focal distance of lens 202, as shown in FIG. 2a, and the maximum value of $\theta$ is sufficiently small (as in this case) to be substantially equal in radians to $\tan \theta$.

It will be noted from equation 1 that the value of d varies linearly with $\theta$. Further, as the value $\theta$ varies during a scan, the position of the point, such as point 216, to which beam 208 converges remains in focal plane 210. This ensures a substantially flat-field image (neglecting the effect of any lens aberration).

Various specific embodiments of scanning ultrasonic embodiments of scanning ultrasonic source and detector 208 are described below in detail. However, for present purposes, all that need be said is that scanning ultrasonic source and detector 208 includes therein, at the very least, (1) transducer means and driving electronics therefor for deriving exploratory pulses of ultrasonic frequency at a suitable repetitionrate, as is known in the art, which exploratory pulses are projected from scanning ultrasonic source and detector as illuminating beam 204; (2) means for controlling, selecting and/or varying the angular orientation with which illuminating beam 204 is projected to thereby control, select and/or vary the angle $\theta$ with which illuminating beam 204 is incident on fixed lens 202, and (3) a detector coupled to or forming part of the transducer for receiving echoes of the exploratory pulses that have been "captured" by fixed lens 202 and received by the transducer of scanning ultrasonic source detector 206. In addition to these essential elements of scanning ultrasonic source and detector 206, block 206 may further include, when required or desired, such means as a collimating lens, a beam expander, a multi-element transducer with suitable controls for selecting a single or a subgroup of elements, an iris (which may be located in the vicinity of fixed lens 202) for adjusting the effective aperture of fixed lens 202 or any other means which may enhance the functional capability of scanning ultrasonic source and detector 206.

In any case, as is conventional, scanning ultrasonic source detector 206 derives an output signal manifesting detected echoes as a function of time, along with suitable scan sync signals which are applied as an input to imaging electronic 218. Imaging electronic, which may be conventional, may include such means as range gates, scan converters, display deflection circuits synchronized with the scanning of illuminating beam 204, etc., to produce at the output thereof signals manifesting the relative intensity at each point of the image and one or more spatial coordinates of this point. As is conventional, this information is applied as the input to display 220, which may be a CRT display. In response thereto, the display derives a visual image of the "scene" within a region of the human patient scanned by converging ultrasonic beam 208.

The smallest detail of the visual image of the "scene" which can be resolved is even smaller than the size of the focused spot in focal plane 210 because fixed lens 202 also operates on the reflected echo returned to scanning ultrasonic source and detector 208, in addition to operating on the original illuminating beam therefrom. In quantitative terms, the diameter $\Delta$ of the focused spot and the size of the smallest resolvable detail $\Delta'$ in the image spot, respectively, are given by the following equations:

$$\Delta = 2.44 \ (f \lambda / A) \text{ and} \qquad (2)$$

$$\Delta' = 1.46 \ (f \lambda / A), \qquad (3)$$

where $\lambda$ is the wavelength of the propagating ultrasonic wave energy, and f and A are respectively the focal length and the aperture of fixed lens 202, shown in FIG. 2a.

Practical values for the aperture A and the focal length f of fixed lens 202, by way of example, are 5 inches and 10 inches, respectively. If, for example, the frequency of the ultrasonic energy is 3MHz, the value of the propagation wavelength is substantially 0.5 mm. Substitution of these example values, in equation 3, indicates that a resolvable image spot diameter $\Delta'$ of 1.46 mm is obtained. By employing a fixed lens 202 having a larger value numerical aperture (i.e. a larger ratio of A/f) and/or employing ultrasonic energy at a frequency higher than 3 MHz, the image resolution capability can be increased even further. In general, depending upon the specific type of tissue being imaged and the depth of the tissue, optimum resolution in the range of 0.5–2.5 mm may be accomodated by a suitable choice of values for the parameters $\lambda$, f and A of equations 2 and 3.

As is known in optics, the depth of field δ is given by the following equation:

$$\delta = 4 \lambda (f/A)^2 \quad (4)$$

It can be seen from equation 4 that the depth of field δ varies inversely with the square of the value of the numerical aperture. In optics, this relationship cannot be practically exploited because the very small wavelength of light (i.e. 0.4–0.7 μm) causes the depth of field for a high numerical aperture lens to become very small. However, in ultrasonics, where the value of the propagating wavelength λ is in the range of 0.15–1.5 mm. (for frequencies of 1–10 MHz), a relatively large depth of field is retained even for a relatively large numerical aperture lens. For instance, in the practical example discussed above, where lens 202 has a focal length f of 10 inches and an aperture A of 5 inches, and the propagating wavelength λ is 0.5 mm., equation 4 shows that the depth of field δ still has a relatively large value of 8 mm (a value more than five times the image spot diameter of 1.46 mm). Further, as can be seen by comparing equation 4 with equations, 2 and 3, the depth of field varies inversely with the square of the numerical aperture, while the spot diameter varies inversely only linearly with the numerical aperture. Thus, if desired, the depth of field can be increased significantly, with only a relatively small price in resolution capability, by a relatively small reduction in the value of the numerical aperture of lens 202.

In fact, by using such means as an iris to stop down the effective aperture of a large aperture lens, a large depth field, relatively low resolution preliminary image may be obtained for the purpose of ascertaining the exact location of a desired target area, so that a fine adjustment may then be made in the relative position of lens 202 with respect to the patient to ensure that the desired target area substantially coincides with the focal plane of lens 202. After this fine adjustment has been made, the iris may be opened fully to permit a high resolution image of the target area to be obtained.

Some portion of the ultrasonic energy of beam 208 passing through the patient is scattered toward and then reflected from points laterally displaced from the one, (such as 216), at which scanning ultrasonic beam 208 is then focused. Receipt and detection of reflections of such scattered ultrasonic energy would give rise to spurious signals. However, the arrangement shown in FIG. 2 and 2a is substantially immune to such spurious signals because any ultrasonic energy reflected from points spaced from spot 216 which are returned to lens 202, in passing through lens 202, derive a beam corresponding to beam 204 oriented at angles displaced from angle 0, shown in FIG. 2a. Therefore, the ultrasonic energy returned to the scanning transducer of block 206, which is detected, is substantially limited to primary reflected ultrasonic energy within the depth of field of each successive focus point, such as point 216, in focal plane 210 during a scan of the target area.

Figure 3:
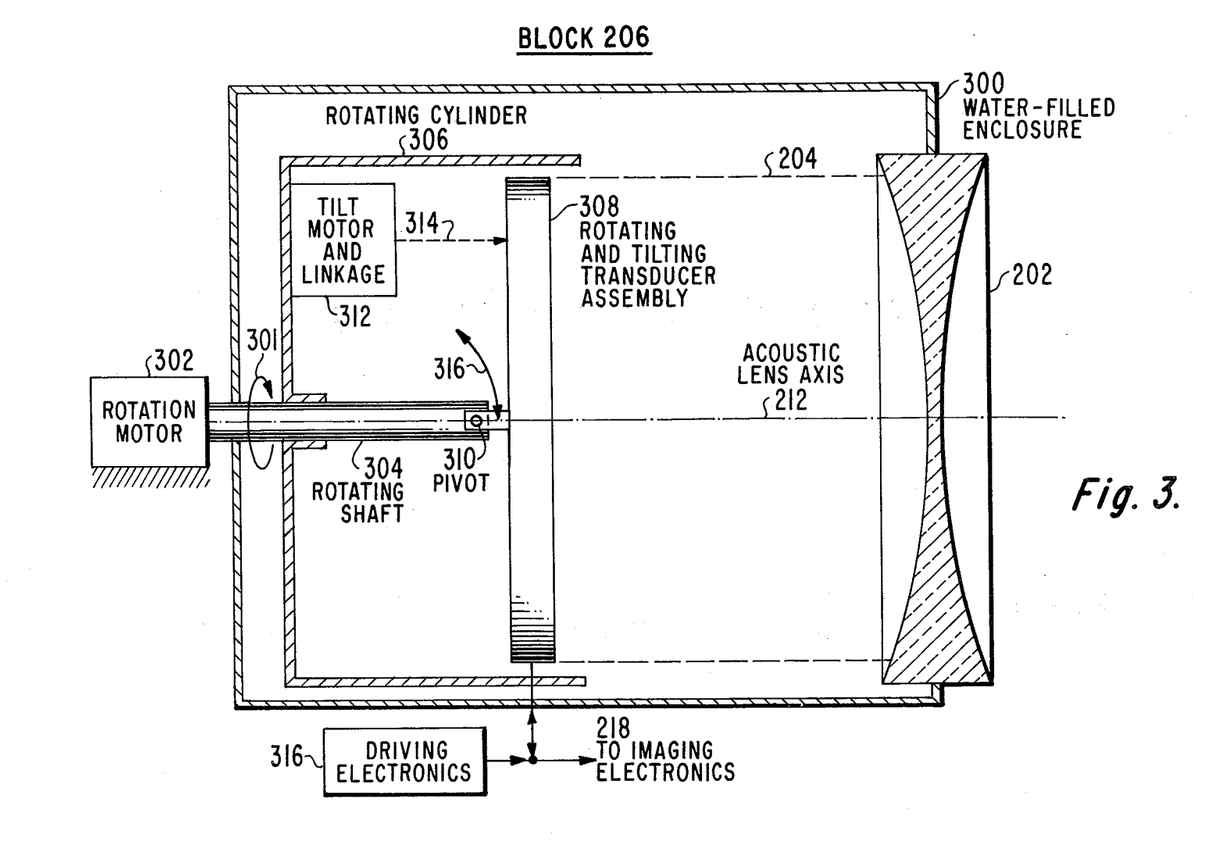
FIG. 3 illustrates a first species of the scanning ultrasonic source and detector of FIG. 2.

Referring now to FIG. 3, there is shown a first embodiment of scanning ultrasonic source and detector 206, which includes water-filled enclosure 300 having a front wall including fixed lens 202. As indicated by arrow 301, stationary rotation motor 302 turns rotating shaft 304 about the acoustic axis 212 of fixed lens 202 at a relatively high, predetermined rate. Secured to rotating shaft 304 and spinning therewith is rotating cylinder 306. Rotating and tilting transducer assembly 308 is tiltably mounted to the distal end of rotating shaft 304 by pivot 310. Tilt motor and linkage 312 secured to rotating cylinder 306 and spinning therewith is mechanically coupled to transducer assembly 308 (as indicated by dashed arrow 314) to effect the tilting back and forth of transducer assembly 308 (as indicated by double-headed arrow 316) through a small angle at a relatively slow second predetermined rate. By way of example, transducer assembly 308 may comprise a relatively large aperture (such as 5 inches) piezoelectric plate. Although not specifically shown, suitable means such as slip rings are provided for electrically coupling the piezoelectric plate of transducer assembly 308 to both driving electronics 316 and imaging electronics 218. Driving electronics 316, as is conventional, supplies short (e.g. 1μs) exploratory pulse signals at a suitable repetition rate to permit a relatively large number of (e.g. 10,000) separate detected sample points to be obtained during a scan of the target area. These detected samples are forwarded as an input to imaging electronics 218. Although not specifically shown, means, such as incremental shaft encoders, supply imaging electronics 218 with suitable scan sync signals from motors 302 and 312. Similarly, the incremental shaft encoder of rotation motor 302 may be used to provide a sync signal to driving electronics 316 for determining the repetition rate of the exploratory pulses. The high-rate rotation together with the lowrate tilt of transducer assembly 308, in the manner described above, causes ultrasonic energy beam 204 to describe a spiral scan format of the focused spot of lens 202. The velocity of ultrasonic energy in water or human tissue is in the order of 1.5 × 10⁶ mm/sec. At this velocity, the time between the transmission of an exploratory pulse and the return of an echo from the focal plane of a lens having a focal length of 10 inches (as assumed above) exceeds 330 microseconds. If a target area scan includes 10,000 sample points, the time for such a scan exceeds 3.3 seconds. While such a target scan interval is relatively short, it is still longer than real time. Therefore, when the arrangement of FIG. 3 is employed, it is advisable that an imaging electronics 218 include a scan converter for storing the target area information derived by the spiral scan and then converting it to a raster scan for display on a CRT. Imaging electronics 218 may also include an appropriate range gate for confining the information reaching the scan converter to the focal plane itself (or some other image plane within the depth of field).

Since the scan interval corresponds to the tilt interval, tilt motor and linkage 312 provides, for the assumed example, a tilt interval that exceeds 3.3 seconds. A tilt interval should preferably contain about 50 revolutions of rotation of transducer assembly 308. Thus, for the assumed example, the spinning rate of rotating shaft 304, rotating cylinder 306 and rotating transducer assembly 308 should have a value somewhat in excess of 1,000rpm, with about 200 exploratory pulses being transmitted during each revolution of transducer 308. In this case, the repetition rate of the exploratory pulse signals applied to the transducer element of transducer assembly 308 by driving electronics 316 is somewhat in excess of 3.3 kHz.

If lens 202 is circularly symmetrical lens, such as a spherical lens, it may be secured directly to rotating cylinder 306, to permit lens 202 to spin about its own acoustic axis 212, without in any way altering its effect on ultrasonic beam 204. In this case, rotating cylinder and spinning lens 202 would form the water-filled enclosure, and enclosure 300 could be dispensed with. Although such spinning of lens 202 about its own acoustic axis is not advised, it is still within the contemplation of the present invention.

As is known in the art, a relatively large aperture beam of ultrasonic energy can be derived from a relatively small aperture ultrasonic transducer (or even a point source of ultrasonic energy) by the use of a suitable acoustic collimating lens and/or reflector together with (if required) suitable beam-expanding lens and/or reflector means. Therefor, the present invention contemplates the substitution of such more complex means for large-aperture transducer assembly 308. Further, as is known in the art, the transducer of assembly 308 may have a predetermined curve surface rather than a plane surface. Still further, although it is preferred that ultrasonic energy beam 204 have a plane wavefront, all that is essential is that lens 202 focus the incident ultrasonic energy beam 204 to a spot in an image plane (as determined by geometric optics from the curvature of the incident ultrasonic energy and the focal length of the lens).

Figure 4:
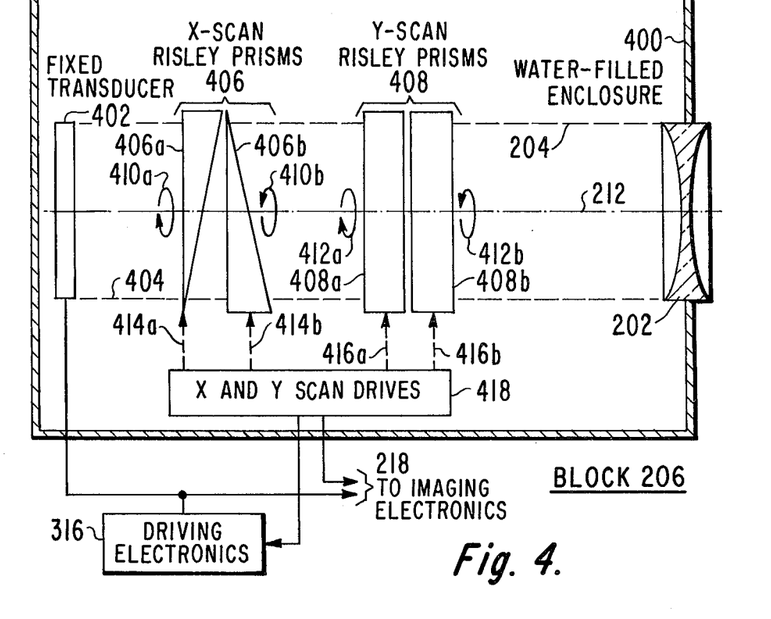
FIG. 4 illustrates a second species of the scanning ultrasonic source and detector of FIG. 2.

Referring now to FIG. 4, there is shown a second embodiment of scanning ultrasonic source and detector 206, which employs a fixed transducer. Specifically, in FIG. 4, block 206 comprises water-filled enclosure having a front wall which includes lens 202. Situated within enclosure 400 is relatively large aperture fixed transducer 402, which may comprise a piezoelectric plate. Fixed transducer 402, in response to exploratory pulse signals applied thereto from driving electronics 316, generates non-scanning ultrasonic energy beam 404. Raster-scanned ultrasonic beam 204, which illuminates lens 202, is derived from non-scanning ultrasonic beam 404 by being serially passed through both a pair of x-scan Risley prisms 406 and a pair of y-scan Risley prisms 408.

As known in the art of optics, a pair of Risley prisms may be used to substantially linearly deflect a beam of wave energy passing therethrough. In particular, one of the prisms of each pair is rotated continuously at a predetermined rate in a clockwise direction while the other prism of each pair is simultaneously rotated at the same predetermined rate in the counter-clockwise direction. That is, in FIG. 4, x-scan prism 406a is rotated at a relatively high first predetermined rate and y-scan prism 408a is rotated at a relatively low second predetermined rate in the clockwise directions, as indicated by arrows 410a and 412a. Simultaneously, x-scan prism 406b is rotated at the first predetermined rate and y-scan prism 408b is rotated at the second predetermined rate in counter-clockwise directions, as indicated by arrows 410b and 412b. This rotation of x-scan prisms 406 and y-scan prisms 408 is achieved by mechanical couplings 414a, 414b, 416a, and 416b from x and y scan drives 418. Drives 418 also supply scan sync signals to imaging electronics 218 and exploratory pulse repetition sync signals to driving electronics 316.

In FIG. 4, the relative assumed position shown for y-scan prisms 408a and 408b, with respect to each other, is the same as the assumed relative position shown for x-scan prisms 406a and 406b, with respect to each other. However, the absolute assumed position of x-scan prisms 406 is in the plane of the paper, while the absolute position of y-scan prisms 408 is in a plane perpendicular to the paper. With prisms 406 and 408 oriented in the assumed positions shown in FIG. 4, (because the deflection of ultrasonic beam 404 caused by prisms 414z and 416a, respectively, is cancelled by the deflection of ultrasonic beam 404 caused by prisms 414b and 416b, respectively) no net deflection of ultrasonic beam 204 occurs. However, counter rotation of prisms 406a and 406b from the assumed position by one-quater cycle (in the direction indicated by arrows 410a and 410b) brings the bases of prisms 406a and 406b into alignment (in a plane parallel to but above the paper) to provide maximum deflection of beam 204 in the x-direction (perpendicular to the paper). At the end of one-half cycle of counter rotation of prisms 406a and 406b (in the direction indicated by arrows 410a and 410b), prisms 406a and 406b again point in opposite directions but now the base of prism 406a is at the bottom of the paper and the base of prism 406b is at the top of the paper. Again, cancellation occurs, and there is no net deflection of ultrasonic energy beam 204. At the end of three-quarters of a cycle of counter rotation of prisms 406a and 406b (in the direction indicated by arrows 410a and 410b), the bases of prisms 406a and 406b are aligned in a plane parallel to but below the paper. This results in a maximum deflection of ultrasonic energy beam 204 in the x-direction. The y-scan prisms 408 operate in a similar fashion, but because of the initial 90° displacement of y-scan prisms 408 with respect to x-scan prisms 406, y-scan prisms 408 deflect ultrasonic beam 204 in the y and $-y$ directions (parallel to the paper) during each cycle of revolution thereof. Thus, each complete revolution of a Risley prism pair results in a pair of linear scans first in a given direction and then in a direction opposite to the given direction.

If each scan of the target area includes 10,000 sample points (as assumed above), a relatively high first predetermined rate for the x-scan of about 900 rpm for Risley prisms 406 and a relatively low rate for the y-scan of about 9 rpm for Risley prisms 408 results in a 3.3 second period raster scan of the target area by the focused beam of ultrasonic energy.

Figure 4A:
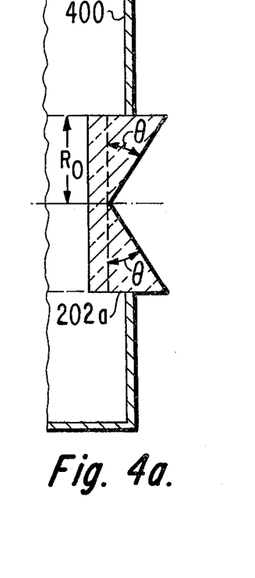
FIG. 4a shows a modification of the arrangement of FIG. 4, employing an axicon as the focusing device.

FIG. 4a shows a modification of the arrangement shown in FIG. 4, in which an acoustic axicon is substituted for lens 202 as the focusing device of block 206. An optical axicon, which may take the form of a cone, described by J. H. McLeod, J. O. S. A. 44, page 592 (1954), when illuminated with a plane wave oriented normal to the axis of the axicon, focuses the incident light along a certain line segment of the axis of the axicon (rather than to a focal point as does a lens). This has the advantage of providing a much greater depth of field than a lens. The only effect of angularly displacing the orientation of the incident plane waves with respect to the normal to the axis of the axicon is to produce an angular shift in the orientation of the focused line segment. Furthermore, for angular displacements of the incident wave at least as large as $\pm 10°$, this angular shift is substantially equal to the incident angular displacement.

In more quantitative terms, if (as shown in FIG. 4a) the radius of the axicon is $R_0$, the angle of the conically-shaped cut away portion of axicon 202a with respect to the normal to the axis thereof is $\theta$, while the normalized index of refraction of the axicon material with respect to that of the surrounding ambient (water) is n and the wavelength of the ultrasonic wave energy is $\lambda$, the range (length of the focused line segment) and beam spot size diameter of the focused line segment are then $$\text{range} = \frac{R_0}{(1-n)\tan\theta} \qquad (5)$$

$$\text{spot size} = \frac{.38\lambda}{(1-n)\tan\theta} \qquad (6)$$

By way of example, if the axicon is composed of polystyrene (n=0.64), wavelength λ is 1mm the radius $R_0$ is about 60 mm. and the axicon angle λ is 26.5°, the beam spot size is substantially constant at 2mm from the plane of the axicon out to about 400 mm.

Although the arrangement shown in FIG. 4a, with axicon 202a situated in the front wall of water-filled enclosure 400, is to be preferred, axicon 202a could be placed between fixed transducer 402 and Risley prisms 406 in the path of ultrasonic wave energy beam 404. In this latter case, the front wall of water-filled enclosure 400 would merely include a window for passing the focused line-segment ultrasonic wave energy.

When an acoustic axicon is employed as the focusing device, it is desirable that display 220 of FIG. 2 include both a B-scan CRT and C-scan CRT. The B-scan, which may use no range gate or may use a relatively wide range gate, provides a display in the plane defined by the relatively fast scan (assumed to be in the x direction) and the axial range direction 212 (z-direction normal to the X-Y plane). Such a B-scan can be accomplished in real time (the approximately 33ms required for one-half revolution of the X-scan Risley prisms 406 in the assumed example). However, a C-scan using a narrow range gate to select the particular X-Y image plane cannot be achieved in real time (i.e. a C-scan in the assumed example takes about 3.3 seconds). Further, by changing the range interval (time delay between the occurrence of an exploratory pulse and the generation of a narrow range gate), the selected X-Y plane displayed as a C-scan may be changed.

Even when the focusing device takes the form of a lens, as in the arrangements of FIGS. 3 and 4, the relatively large depth of field of the acoustic lens, set forth above in equation 4, makes it desirable to include both a B-scan CRT and a C-scan CRT in display 220. Alternatively, by employing the imaging electronics arrangement shown in FIG. 4b, it is possible to provide an isometric three-dimensional display on a single CRT of a selected target volume ultrasonically scanned by the arrangement of FIG. 4 or FIG. 4a.

Figure 4B:
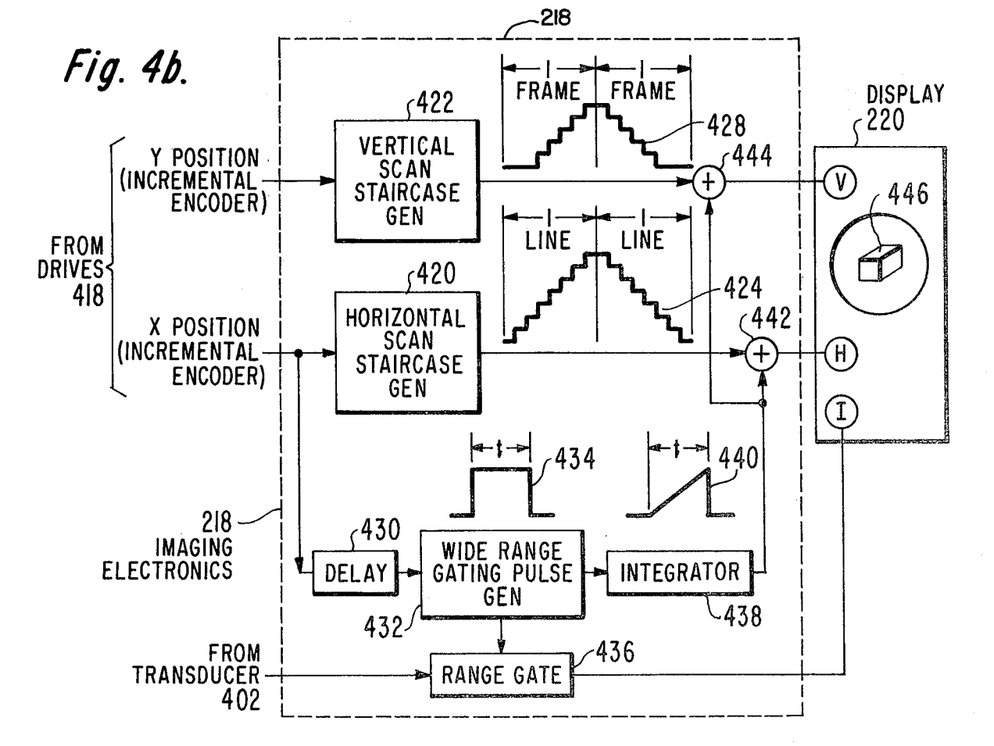
FIG. 4b shows a species of the imaging electronics of FIG. 2 that may be employed with the arrangement of FIG. 4 to provide isometric display of a three dimensional region of the internal structure being imaged.

More specifically, as shown in FIG. 4b, imaging electronics 218 may comprise horizontal scan staircase generator 420 and vertical scan staircase generator 422. An encoder incorporated in X and Y scan drives 418 applies each of a series of X position pulses as an input to horizontal scan staircase generator 420, each such position pulse corresponding to a predetermined angular increment of X-scan Risley prisms 406. In a similar manner, each of a series of Y position pulses corresponding to a predetermined angular increment of Y-scan Risley prisms 408 is applied as an input to vertical scan staircase generator 422. Horizontal scan staircase 420 may include a reversible counter and a digital-to-analog converter for producing as an output staircase wave 424 during each revolution of X-scan Risley prisms 406. In a similar manner, vertical scan staircase generator 422 produces as an output staircase wave 426 during each revolution of Y-scan Risley prisms 408.

The X position incremental encoders also are utilized in FIG. 4 to synchronize the repetition period of the exploratory pulses applied to transducer 402 by driving electronics 316. Therefore, the duration of each step of staircase of wave 424 is equal to one repetition period of the exploratory pulses. Further, by generating each Y-position pulse from drive 418 at the end of each one-half cycle of X-scan Risley prisms 406, each step of staircase wave 428 corresponds in duration with a "one-line" period of staircase wave 424. Similarly, one-half cycle of Y-scan Risley prisms 408 corresponds in duration with one frame of the display.

Each X position pulse is also passed through delay 430, which provides a delay equal in duration to the time between the transmission of an exploratory pulse from transducer 402 and the receipt by transducer 402 of an echo returned from the closest portion of the internal structure volume to be displayed. The delayed position pulse triggers wide range gating pulse generator 432 to produce a rectangular pulse waveform 434 having a duration t corresponding to the depth of the internal structure volume to be displayed. Pulse 434 is used directly to open range gate 436, thereby permitting only the detected echoes returned from the depth to reach the intensity-control (z-axis) of display 220, as is conventional. However, in addition, gating pulse 434 is applied to integrator 438 to produce as an output ramp 440 during interval t of each range period. Therefore, the duration of ramp 440 may be only a small portion of each relatively short step of staircase waveform 424, as well as each relatively long step of staircase waveform 428. Summing operational amplifier 442 is used to add ramp 440 to staircase wave 424 and apply its output to the horizontal scanning input of display 220. In a similar manner, operational amplifier 444 is used to add ramp 440 to staircase wave 428 and apply its output to the vertical scanning input of display 220. As indicated by cube 446, the addition of ramp 440 to the horizontal and vertical scan results in a three-dimensional isometric format for the display of the intensity-modulated range information of the ultrasonically scanned volume of internal structure. This three-dimensional isometric displayed format is an aid in visualizing the internal structure of complex shapes, such as various shapes of human tissue.

Neither of the embodiments for scanning ultrasonic source and detector 206, shown in FIGS. 3, 4, 4a and 4b (or in fact, any point-at-a-time scanningsystem) is capable of providing a C-scan in real time, due to the relatively long round-trip time interval (e.g. 330 μs) between the transmission of an exploratory pulse and the return of an echo from the focal plane of the lens. However, by employing either time division or space division multiplex techniques, an entire line section of the target area can be effectively sampled point by point in a period between one and two times a round trip interval. Thus, if the target area comprises 100 line sections, with each line section comprising 100 sample points, and the round trip interval is 330 μs, an entire scan of the target area can be achieved with a period between 33 and 66 milliseconds. Therefore, the high-resolution imaging techniques of the present invention are compatible with real-time scanning of the target area.

Figure 5:
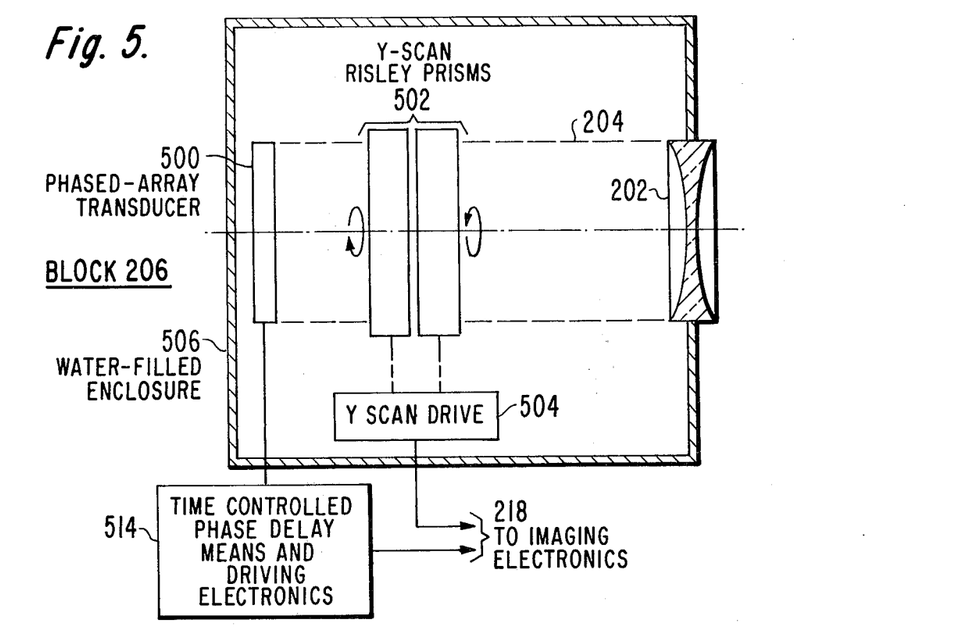
FIGS. 5 and 5a illustrate a third species of the scanning ultrasonic source and detector of FIG. 2.
Figure 5A:
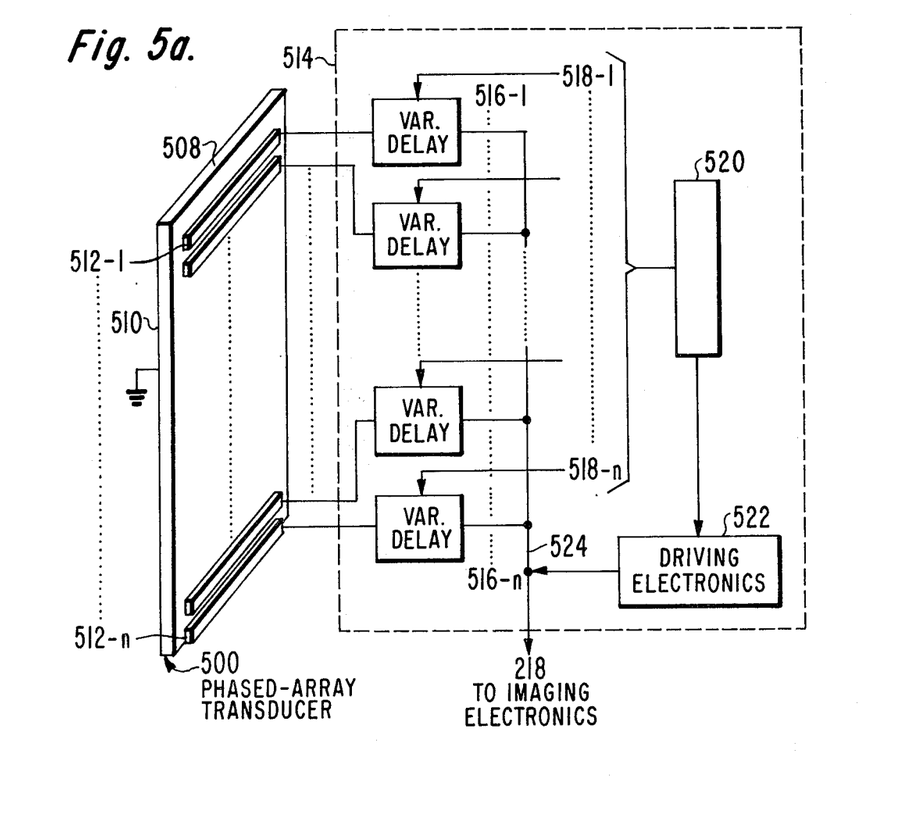

Referring now to FIGS. 5 and 5a, there is shown an embodiment of scanning ultrasonic source and detector 206 which employs time division multiplex techinques for achieving real time scanning of the target area. The embodiment of scanning ultrasonic source and detector 206, shown in FIGS. 5 and 5a, comprises x-scan phased array transducer 500, y-scan Risley prisms 502 and y- scan drive 504 within a water-filled enclosure 506 having lens 202 incorporate in its front wall. X-scan phased array transducer 500, shown in more detail in FIG. 5a, preferably comprises piezoelectric plate 508 having one face thereof covered with grounded electrode 510 and the other face thereof covered with an array of line-section electrodes 512-1 . . . 512-n. Time-controlled phase-delay means and driving electronics 514 supplies exploratory pulses to phased array transducer 500 and forwards detected echoes and X-scan sync signals to imaging electronics 218. Y-scan drive 504 supplies the Y-scan sync signals to imaging electronics 218.

Reference is made to "Microwave Scanning Antennas", Volume 3, Edited by R. C. Hansen, and published by the Academic Press, N.Y. in 1964, which describes in detail phased-array techinques, useful in radar. In particular, the direction of the beam of wave energy from a phased-array is a predetermined function of (1) the known distance between adjacent sections of the array, (2) the known velocity of the wave energy in the propagating medium, and (3) the selectively-controlled difference in phase between the driving wave energy applied to each adjacent pair of array section. Therefore, phased-array scanning techniques are just as applicable to ultrasonic wave energy as to microwave electromagnetic wave energy.

FIG. 5a shows schematically an embodiment of time-controlled phase-delay means and driving electronics 514. In particular, associated with each line section 512-1 . . . 512-n of phased-array transducer 500 is a corresponding one of signal-controlled bilateral variable delay devices 516-1 . . . 516-n. Each of these variable delay devices effectively inserts an amount of time delay in a signal passing therethrough in accordance with a control signal on the corresponding one of control leads 518-1 . . . 518n applied thereto from time control 520. Variable delay devices 516-1 . . . 516-n may be analog devices, such as tapped lines. However, in practice, they would normally be digital devices, such as any of those described in Volume 3 of the aforesaid "Microwave Scanning Antennas." In operation, driving electronics 522, under the control of time control 520, applies a predetermined number, e.g. 100, exploratory pulses in succession to phased-array transducer 500 through common lead 524 and variable delay devices 516-1 . . . 516-n. Further, time control 520 provides a different set of control signals 518-1 . . . 518-n for each successive exploratory pulse to appropriately sweep the ultrasonic beam transmitted by transducer 500 in the X direction. The total time of such a sweep should preferably be as short as possible (i.e. the duty-cycle of the exploratory pulses should be as high as possible) and in no event can be longer than the round-trip travel time to the target area. Thus, if a sweep is composed to 100 exploratory pulses, each having a width of 1μs and the round trip travel time between the transmission of an exploratory pulse and the receipt of an echo in response thereto is 330μs (as assumed above), a minimum sweep period with high duty-cycle exploratory pulses must exceed 100μs in duration while a maximum sweep period must be less than 330μs in duration. At the end of a round-trip interval, (i.e. 330μs) variable delay devices 516-1 . . . 516-n under the control of signals 518-1 . . . 518-n from time control 520 again sweep transducer 500 in an identical manner to detect returned echoes and apply the echoes to imaging electronics 218 over common lead 524. Thus, it takes a time interval between one and two times the round trip travel time between the transmission of an exploratory pulse and the return of its responding echo to scan one entire line of the target area in the X direction. In more quantitative terms, $$T_x = T_r + T_s \tag{5}$$

$$n_x t < T_s < T_r \tag{6}$$

where $T_X$ is the time to scan a line of the target area in the X direction, $T_r$ is the round trip time, $T_s$ is the sweep period, $n_x$ are the number of sample points in a scan line in the X direction and t is the width of an exploratory pulse. In the assumed example, where $T_r$ is 330μs, $n_x$ is 100 and t is 1μs, the value of $T_X$ is greater than 430μs but less than 660μs. Further, if a total scan of the target area is composed of 100 lines, a scan period is longer than 43 milliseconds but less than 66 milliseconds (i.e. Y-scan Risley prisms 502 are driven at a rate between approximately 900–1400 rpm). This provides a real time frame rate of between 14 and 24 frames per second.

Figures 6, 6A:
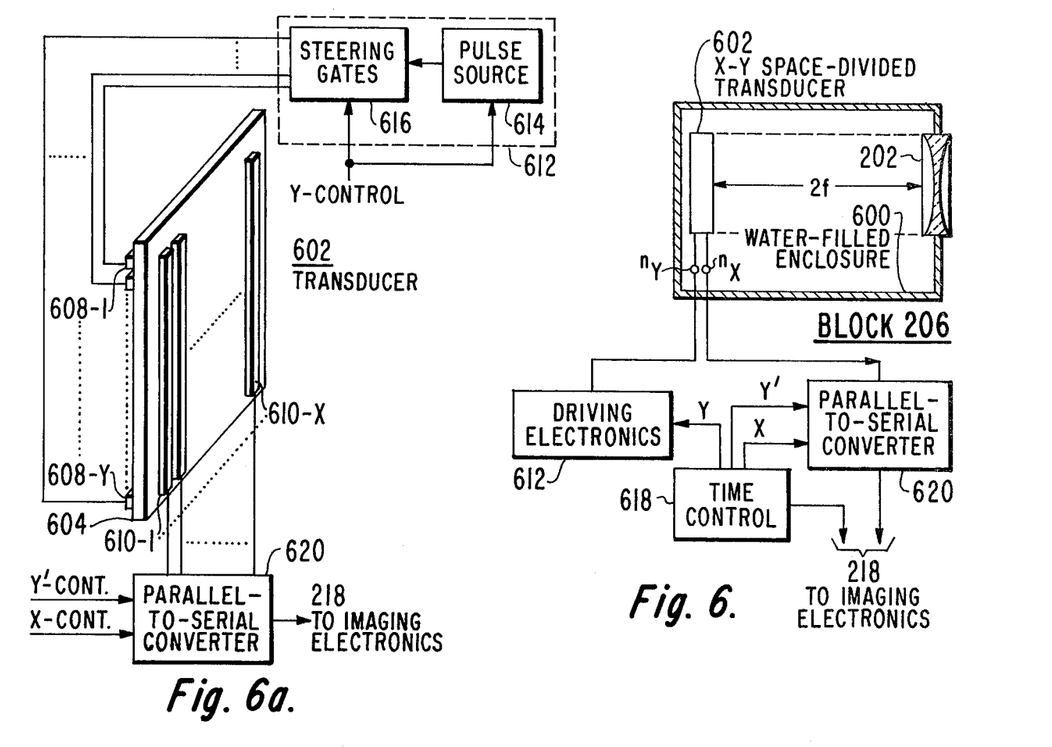
FIGS. 6 and 6a illustrate a fourth species of the scanning ultrasonic source and detector of FIG. 2.

Referring now to FIGS. 6 and 6a, there is shown a space-divided embodiment of scanning ultrasonic source and detector 206 for providing real-time scanning of the target area. Lens 202 is incorporated into the front wall of water-filled enclosure 600. Immersed in water-filled enclosure 600 is X-Y spaced-divided transducer 602. Transducer 602 is preferably situated at a distance from lens 202 equal to twice its focal length (2f), as indicated in FIG. 6, so that points on transducer 602 are imaged with unity magnification on a target area plane situated at a distance beyond lens 202 also equal to 2f. Similarly, points in the target area will be imaged with unity magnification at transducer 602. As shown in FIG. 6a, transducer 602 comprises piezoelectric plate 604 having a first set of driving line-section electrodes 608-1 . . . 608-y on the left surface thereof and a second set of sensing line-section electrodes 610-1 . . . 610-x on the right face thereof. As shown, the second set of electrodes is orthogonally oriented with respect to the first set of electrodes to thereby define (x . y) cross points therebetween. Each of these cross points corresponds to a sampling point of the target area. If, as has been assumed, x and y both have a value of 100, the total number of sampling points in the scan of the target area is 10,000.

Driving electronics 612 for energizing transducer 602 comprises pulse source 614 and steering gate 616. More specifically, under the control of Y signals from time control 618, steering gate 616 operates as a commutator to selectively supply successive exploratory pulses in sequence to each of driving electrodes 608-1 . . . 608y, while simultaneously grounding all the non-selected remaining ones of this first set of electrodes. At the time an exploratory pulse is applied to driving electrodes 608-1 . . . 608-y, sensing electrodes 610-1 . . . 610-x are also grounded. This results in a narrow (e.g. 1 mm.) line beam of ultrasonic energy consisting of the energy launched from each of the cross-points of the then-selected one of driving electrodes 608-1 . . . 608-y.

Because each sampling point of the target area is imaged at a corresponding cross-point of the transducer in the arrangement of block 206 shown in FIGS. 6 and 6a, the round-trip travel time between the transmission of an exploratory pulse and the receipt of an echo from the target area in response thereto is twice that of the previously-discussed embodiments of block 206. More specifically, if the target area is situated ten inches beyond lens 202 (i.e. 2f=10 inches), as has been assumed, the total distance between transducer 602 and the target area is 20 inches. Therefore, the round trip travel time is in the order of 660 μs (assuming a velocity of 1500m/s for the ultrasonic energy in the propogating medium).

Y controls signals are applied to pulse source 614 in steering gates 616 at the beginning of a Y repetition period equal to or slightly greater than the round-trip travel time (660 μs) to cause each respective driving electrode 608-1 ... 608-y to launch an exploratory pulse of ultrasonic energy in consecutive order at substantially 660 μs intervals.

Parallel-to-serial converter 620, which includes a set of x storage elements, a set of input gates under the control of Y' signals from time control 618, for applying the signals sensed by the sensing electrodes 610 ... 610-x to the corresponding storage elements at or near the end of each Y (660 μs) period (but grounding electrodes 610-1 ... 610-x at other times), and a steer-out circuit under the control of X-signals from time control 618 for sequentially reading out all the stored signals on the set of storage elements during the following Y period to thereby apply a serial stream of x (e.g. 100) sample point signals to imaging electronics 218 during that Y period. Time control 618 also supplies scan sync signals to imaging electronics 218. Thus, the scan of the entire target area takes (y+1) Y periods or, in the assumed example, 66.66ms. This is a real-time frame rate of 15 scans of the target area per second.

At the end of any Y period, while parallel-to-serial converter 620 is sampling the echoes returned from the target area in response to the exploratory pulse transmitted from a particular one of driving line-section electrodes at the beginning of that Y period, it may be desirable for steering gate 616 to momentarily disconnect electrodes 608-1 ... 608-y (i.e. allow electrode 608-1 ... 608-y to float), in order to reduce the effective shunting parasitic load impedance between sensing electrodes 610-1 ... 610-x and ground. This shunting load impedance tends to reduce the effective sensitivity and raise the effective signal-to-noise ratio of the sensed signals forwarded by sensing electrodes 610-1 ... 610-x to the storage elements of parallel-to-serial-converter 620. In any event, all other things being equal, the greater the number x-y cross-points, the greater is the effect of the shunting load impedance.

Figure 6B:
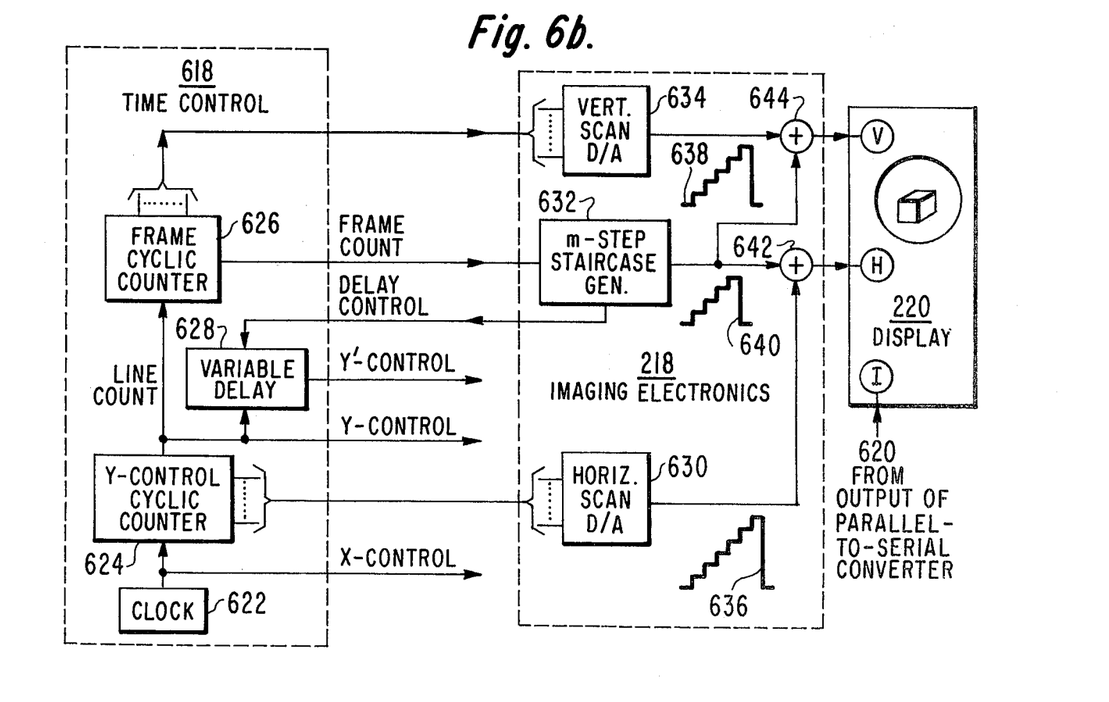
FIG. 6b illustrates a species of the imaging electronics of FIG. 2 and a species of the time control of FIG. 6 which may be employed with the arrangement of FIG. 6 to provide an isometric display of a three dimensional region of the internal structure being imaged.

Referring now to FIG. 6b, there is shown a specific embodiment of time control 618 and imaging electronics 218 which provides an isometric three-dimensional display on a single CRT of a selected target volume ultrasonically scanned by the arrangement of FIGS. 6 and 6a. As shown in FIG. 6b, time control 618 may include clock 622 for generating X-control signals at a repetition rate equal to that of the serial stream of y sample point signals from parallel-to-serial converter 620. If, as assumed, there are 100 sample points within each Y period of 660 μs, clock 622 operates at a repitition frequency of about 150 kHz. The output from clock 622 is applied as an input to Y-control cyclic counter 624, which recycles at the end of each Y period (i.e., 100 counts in the assumed example) to provide a line count output at 1.5 kHz. This line count output, besides being applied as an input to frame cyclic counter 626 and variable delay means 628, corresponds to the Y-control output from time control 618. In addition, the accumulated count within a cycle of Y-control cyclic counter 624 is applied as an input to horizontal scan digital to analog converter 630 of imaging electronics 218.

Frame cyclic counter 626 recycles after each frame (i.e., 100 lines in the assumed example) to apply a frame count input into m-step staircase generator 632 of imaging electronics 218. In addition, frame cyclic counter 626 applies a signal representative of the accumulated line count within a cycle as an input to vertical scan digital-to-analog converter 634 of imaging electronics 218.

The output from horizontal scan D/A is staircase wave 636, in which the duration of each step is equal to one clockperiod and the duration of the entire wave is equal to that of a line. Vertical scan D/A produces as an output staircase wave 638, in which the duration of each step is equal to that of a line and the duration of the entire wave is equal to that of a frame.

The m-step staircase generator 632 comprises a cyclic counter which recycles every m frame counts, analog or digital means responsive to the accumulated count in a cycle of this counter for applying a delay control signal to variable delay means 628 and a digital-to-analog converter for deriving staircase wave 640 in accordance with the accumulated count registered in the counter. Staircase wave 640 consists of m steps each having a duration equal to a frame count.

Staircase wave 640 is added to horizontal staircase wave 636 in summing operational amplifier 642 and applied to the horizontal scanning input of display 220. Further, staircase wave 640 is added to vertical staircase waves 638 in summing amplifier 644 and applied to the vertical scanning input of display 220. The serial stream of x sample signals forming the outputs from parallel-to-serial converter 620 is applied to the intensity-control input of display 220.

During a frame corresponding to the lowest step of staircase wave 640, the delay control signal is such as to cause variable delay 628 to provide a minimum delay between the occurrence of each Y-control signal (corresponding to the transmission of an exploratory pulse) and the occurrence of a Y' control signal (which opens the gates controlling the storage of detected echo signals by parallel-to-serial converter 620). Thus, the stream of x sample signals applied to the intensity-control input of display 220 corresponds with the nearest image plane of the internal structure target volume being displayed. Further, this nearest image plan is displayed in a C-scan format determined by the plurality of horizontal staircase waves 636 and the single vertical staircase wave 638 which occur within the duration of this lowest step of staircase wave 640. The next frame, which occurs within the duration of the second step is displayed as a second C-scan which is positioned slightly to the right of and above the first C-scan. At the same time, the value of the delay control signal during the second step of staircase wave 640 results in echoes from a somewhat more distant image plane of the internal structure target volume being applied to the intensity-control input of display 220 by parallel-to-serial converter 620. This process, which is repeated for each of the m steps in staircase waveform 640, results in an isometric three-dimensional display of the internal structure target volume on display 220.

By way of example, if the difference in delay provided by variable delay means 628 between each pair of adjacent steps corresponds with a distance of about 2 mm (which is close to the limit of depth resolution at the ultrasonic wavelengths employed) and the value of m is 25, a three-dimensional isometric display of about a two-inch depth internal structure target volume is achieved.

Figure 7:
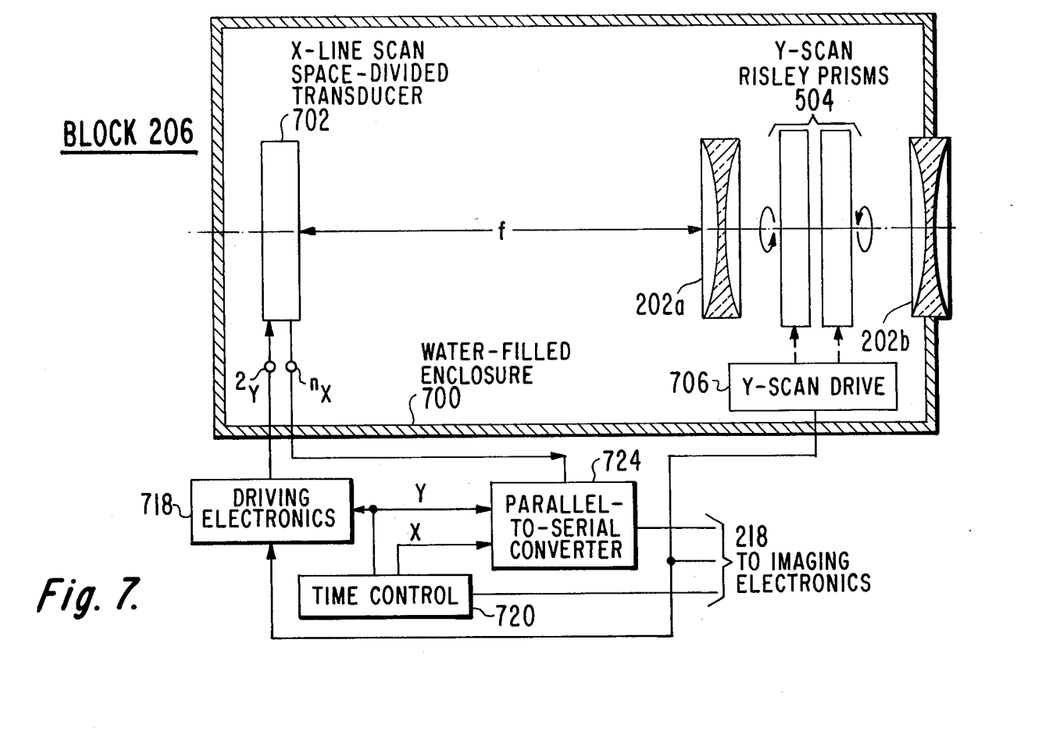
FIGS. 7 and 7a show a fifth species of scanning ultrasonic source and detector 206.
Figure 7A:
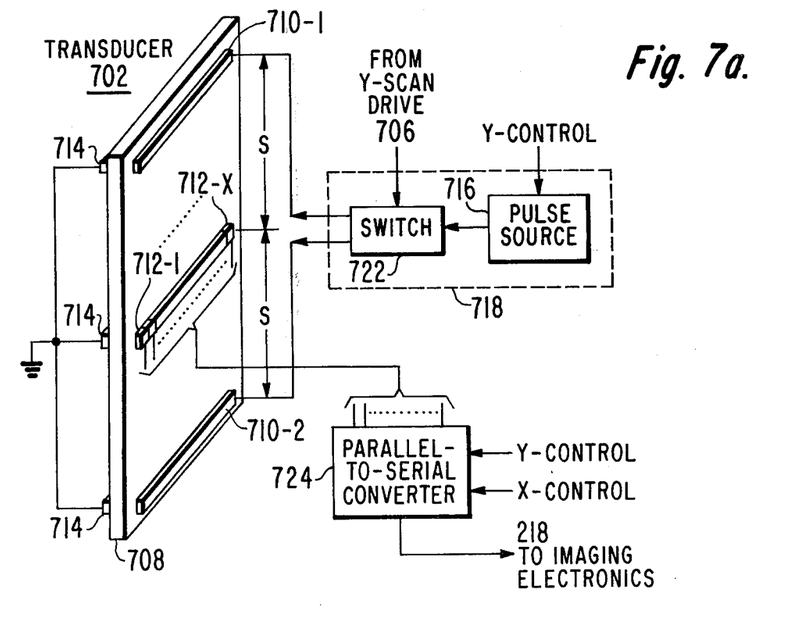

FIGS. 7 and 7a show an embodiment of scanning ultrasonic source and detector 206, which operationally is the functional equivalent of the embodiment shown in FIGS. 6 and 6a, but which inherently exhibits a much lower parasitic shunting load impedance.

Referring to FIG. 7, immersed in water-filled enclosure 700 are X-line scan space-divided transducer 702 and Y-scan Risley prisms 704 coupled to Y-scan drive 706. Sample points of the target area are imaged at corresponding points of transducer 702 by a lens system composed of two spaced lenses 202a and 202b, situated, as shown, on either side of Y-scan Risley prisms 704. This imaging results from the fact that lens 202b, which is incorporated in the front wall of water-filled enclosure 700, has its focal plane situated in coincidence with the target area, and transducer 702 is located in the focal plane of lens 202a. The use of a two-lens system to provide imaging of the sample points of the target area on transducer 702 is to be preferred in the arrangement of FIG. 7 to the single lens approach used in FIG. 6 because the two-lens approach insures less distortion because the Y-scan Risley prisms are illuminated with paraxial plane-wave acoustic energy, rather than spherical wave energy from a linearly scanned point source.

Referring now to FIG. 7a, transducer 702 comprises piezoelectric plate 708 having two driving line-section electrodes 710-1 and 710-2 mounted on the right face thereof. Halfway between driving line-section electrode 710-1 and 710-2, at a distance "s" from each, is a linear array of individual sensing electrodes 712-1 . . . 712-x. Mounted on the left face of piezoelectric plate 708, in corresponding relationship with each of driving line-section electrodes 710-1 and 710-2 and the linear array of sensing electrodes 712-1 . . . 712-x are grounded line-section electrodes 714, as shown. Pulse source 716 of driving electronics 718, in response to Y control signals from time control 720, applies a series of exploratory pulses to a selected one of driving electrodes 710-1 and 710-2 through switch 722 at a repetition rate which is substantially equal to the round trip travel time between the transmission of an exploratory pulse and a receipt of an echo from the target area response thereto (e.g. 660 μm). Switch 722 selects the one of the driving electrodes 710-1 and 710-2 which an exploratory pulse is forwarded in response to a control signal from Y-scan drive 706 applied thereto.

Y-scan Risley prism 704 are continuously rotating during the time an exploratory-pulse is traveling toward the target and during the time that an echo therefrom is traveling back toward transducer 702. Therefore, an echo responsive to an exploratory pulse launched from a selected one of driving electrodes 710-1 and 710-2 does not return to that selected driving electrode, but is incrementally deflected in the Y direction by a given distance which is determined by the speed of rotation of Y-scan Risley prism 704 and the round-trip travel time to the target area. The spacing distance between the linear array of sensing electrode 712-1 . . . 712-x and either one of the driving electrode 710-1 and 710-2 is chosen to be equal to this given distance. Furthermore, during a first half of each cycle of Y-scan Risley prism 704, a beam of acoustic energy passing therethrough is deflected in the Y-direction from top-to-bottom. However, during the remaining half of each cycle of location of Y-scan Risley prism 704, a beam of acoustic energy passing therethrough is deflected in the Y-direction from bottom-to-top. The control signal applied to switch 722 from Y-scan drive 706 causes exploratory pulses to be forwarded to driving electrode 710-1 and driving electrode 710-2 to be grounded during the half-cycle of rotation of Y-scan Risley prism 704 when the acoustic beam is being deflected from top-to-bottom. Similarly, exploratory pulses are applied to driving electrode 710-2 and driving electrode 710-1 is grounded by switch 722 during those half-cycles of Risley prism 704 during which the acoustic beam is deflected from bottom-to-top. In either case, returning echoes from the target area are incident on the linerarray of sensing electrode 712-1 . . . 712-x.

Assuming that the cycle period of Y-scan Risley prism 704 is not exactly equal to an even integral multiple of the repetition period of the exploratory pulses, a different set of X-lines of the target area will be sample during consecutive half-cycles of rotation of Risley prism 704. That is, an inter-laced raster scan of the target area is achieved.

Parallel-to-serial converter 724, which is structurally and functionally identical to parallel-to-serial converter 620, described above, the end of each Y period (i.e. exploratory pulse repetition period) samples in a parallel and stores all the line of target area echo signals then being received by sensing electrode 712-1 . . . 712-x, and then converts the stored signals into a corresponding serial stream during the following Y periods.

Ideally, lens 202 in FIG. 6 images flat transducer 602 in a flat image plane and lenses 202a and 202b in FIG. 7 images flat transducer 702 in a flat image plane. However, as is known in the optical art, conventional spherical lenses. exhibit various forms of aberration. Further, the magnitude of these aberrations tends to increase for large aperture lenses, particularly when the object (transducer) occupies a relatively wide field (which is the case in FIGS. 6 and 7).

An especially troublesome aberration to which the arrangements of FIGS. 6 and 7 are subject is the imaging of respective flat transducers 602 and 702 in a concavely curved image plane. One way of overcoming this problem is to provide lens 202 of FIG. 6 and lenses 202a and 202b of FIG. 7 with appropriate complex curvatures derived by computer-controlled ray tracing techniques, known in the art. However, machining large-aperture acoustic lenses with such complex curvatures is both difficult and expensive. A simpler and less expensive solution to this problem is shown in FIGS. 8a and 8b.

Figure 8A:
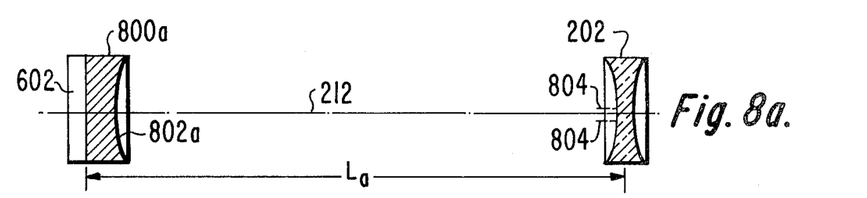
FIG. 8a shows a modification of the arrangement of FIG. 6 for minimizing the effect of those lens aberration causing curvature of the image field.
Figure 8B:
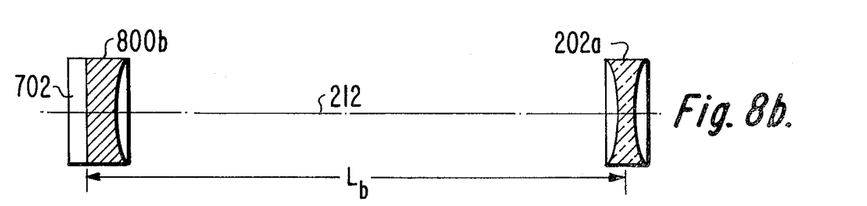
FIG. 8b shows a corresponding modification of the arrangement of FIG. 7.

Referring to FIGS. 8a, corrector plate 800a is disposed, as shown, between transducer 602 and lens 202 in substantial contact with the front surface of transducer 602. Transducer 602 has a relatively high acoustic impedance relative to that of water, the propagating medium. Therefore, corrector plate 800a should be composed of a material exhibiting an acoustic impedance intermediate that of transducer 602 and water. Preferably, the acoustic impedance of corrector plate 800a should be close to the geometric mean between that of transducer 602 and water to provide optimum impedance matching for the ultrasonic wave energy. In practice, corrector plate 800a may be made out of the same material, such as a plastic like polystyrene or methylmethacrylate, as that of acoustic lens 202. However, preferably, corrector plate 800a should be composed of a metal, such as aluminum, which exhibits an acoustic impedance to the propagating ultrasonic waves closer to that required for optimum impedance matching than the acoustic impedance exhibited in plastic.

Corrector plate 800a has a concave front surface 802a, so that it operates as an acoustic condensing lens for (1) retaining an increased portion of the ultrasonic wave energy emitted by transducer 602 within the aperture of lens 202 to thereby increase the ultrasonic wave energy efficiency of the system and, more important, (2) concentrating a very large proportion of the total ultrasonic wave energy illuminating large aperture lens 202 in the small aperture central region 804 thereof surrounding axis 212. Therefore, the large aperture lens 202 provides the required high resolution capabilities with which the acoustic wave energy is focused in the image plane, while, at the same time, the concentration of the ultrasonic wave energy by corrector plate 800a within small aperture region 804 of lens 202 minimizes any undesired curvature of the image plane.

Where cost is no object, the curvature of surface 802a and/or the surfaces of lens 202 can be tailored by ray-tracing techniques to substantially eliminate one or more of the aberrations normally produced by a large aperture lens. However, when both lens 202 and corrector plate 800a have inexpensively produced spherical surfaces, the undesired curvature of the image plane still can be substantially eliminated by providing the condensing lens formed by corrector plate 800a with a focal length substantially equal to distance $L_a$ between the principal plane of corrector plate 800a and that of acoustic lens 202.

The arrangement of FIG. 6 employs a single lens 202 while the arrangement in FIG. 7 employs two spaced lenses 202a and 202b. As shown in FIG. 8b, the condenser lens formed by corrector plate 800b associated with transducer 702 of FIG. 7 has a focal length equal to the distance $L_b$ between the principal plane of corrector plate 800b and the closer acoustic lens 202a of FIG. 7, to thereby concentrate the acoustic wave energy illuminating lens 202a in the central region thereof surrounding axis 212. In all other respects, the arrangement shown in FIG. 8b is substantially identical to that shown in FIG. 8a, described above.

What is claimed is:

1. Apparatus for use in an ultrasonic pulse-echo system capable of displaying an image of certain internal structure of a visually opaque object being scanned with ultrasonic wave energy, said apparatus comprising:

an acoustic focusing device occupying a given aperture which aperture remains substantially fixed in position with respect to said object while said object is being scanned, and ultrasonic beam forming means including transducer means generating successive pulses of ultrasonic wave energy and beam scanning means for illuminating said certain internal structure through said focusing device with a scanning focused beam of said pulsed ultrasonic wave energy, said transducer means being situated remotely from both said focusing device and from said internal structure for receiving and detecting a signal portion of said focused beam reflected from said certain internal structure and returned through said focusing device to said transducer means after a time delay proportional to the distance between said remotely situated transducer means and said certain internal structure.

2. The apparatus defined in claim 1, wherein said ultrasonic beam forming means comprises an enclosure filled with an ultrasonic wave propagating medium, at least a portion of said focusing device being incorporated in a front wall of said enclosure, said transducer being situated within said enclosure a given distance behind said focusing device for illuminating said focusing device with an incident beam of ultrasonic wave energy, said scanning means controlling the angular orientation of said incident beam with respect to said focusing device.

3. The apparatus defined in claim 2, wherein said focusing device comprises an acoustic lens having a large numerical aperture, mounted in said front wall of said enclosure.

4. The apparatus defined in claim 2, wherein said scanning means comprises means for pivotally mounting said transducer at the end of a shaft and means for rotating said shaft at a relatively high speed while simultaneously tilting said transducer about its pivot at a relatively low speed to cause said angular orientation of said incident beam to define a spiral scan.

5. The apparatus defined in claim 2, wherein said scanning means comprises at least one pair of Risley prisms situated in front of said transducer in the path of said beam, said one pair of Risely prisms being oriented to cause said incident beam to linearly scan back and forth in a given linear direction in response to counter rotation of said Risley prisms of said one pair with respect to each other and means for counter rotating said Risley prisms of said one pair at a first given speed.

6. The apparatus defined in claim 5, wherein said scanning means further comprises another pair of Risley prisms situated in front of said transducer in the path of said beam, said other pair of Risley prisms being oriented to cause said incident beam to linearly scan back and forth in a second linear direction orthogonal to said given linear direction in response to counter rotation of said Risley prisms of said other pair with respect to each other and means for counter rotating said Risley prisms of said other pair of second given speed.

7. The apparatus defined in claim 6, wherein said second given speed is sufficiently higher than said first given speed to cause said incident beam to define an x-y raster scan at a frame rate determined by said first given speed and a line rate determined by said second given speed.

8. The apparatus defined in claim 1, wherein said incident beam has a plane wavefront.

9. The apparatus defined in claim 1, wherein said given aperture occupied by said acoustic focusing device is of at least inches in size.

* * * * *

UNITED STATES PATENT AND TRADEMARK OFFICE
CERTIFICATE OF CORRECTION

PATENT NO. : 4,131,021

DATED : December 26, 1978

INVENTOR(S): Reuben Saul Mezrich, et al

It is certified that error appears in the above-identified patent and that said Letters Patent is hereby corrected as shown below:

Column 3, line 7, "focusing" should read --forming--
Column 3, line 9, "illustrating" should read --illuminating--
Column 7, line 53, "0" should read --θ--
Column 11, line 9, "λ" should read --θ--
Column 18, line 13, "linerarray" should read --linear-array--

Signed and Sealed this

First Day of May 1979

[SEAL]

Attest:

RUTH C. MASON
Attesting Officer

DONALD W. BANNER
Commissioner of Patents and Trademarks